(12) United States Patent
Huang

(10) Patent No.: US 10,670,517 B2
(45) Date of Patent: Jun. 2, 2020

(54) WAVELENGTH MODULATION SPECTROSCOPY GAS SENSOR CALIBRATION

(71) Applicant: NEC LABORATORIES AMERICA, Princeton, NJ (US)

(72) Inventor: Ming-Fang Huang, Princeton, NJ (US)

(73) Assignee: NEC Corporation (JP)

( * ) Notice: Subject to any disclaimer, the term of this patent is extended or adjusted under 35 U.S.C. 154(b) by 0 days.

(21) Appl. No.: 15/996,453

(22) Filed: Jun. 2, 2018

(65) Prior Publication Data

US 2019/0170638 A1 Jun. 6, 2019

Related U.S. Application Data

(60) Provisional application No. 62/514,036, filed on Jun. 2, 2017.

(51) Int. Cl.
| | |
|---|---|
| *G01N 21/27* | (2006.01) |
| *G01N 33/00* | (2006.01) |
| *G01N 21/59* | (2006.01) |
| *G01N 21/39* | (2006.01) |
| *G01N 21/3504* | (2014.01) |

(52) U.S. Cl.
CPC .......... *G01N 21/274* (2013.01); *G01N 21/39* (2013.01); *G01N 21/59* (2013.01); *G01N 33/00* (2013.01); *G01N 33/004* (2013.01); *G01N 21/3504* (2013.01); *G01N 2201/1241* (2013.01); *G01N 2201/12746* (2013.01)

(58) Field of Classification Search
CPC ...... G01N 21/274; G01N 21/39; G01N 21/59; G01N 33/00; G01N 33/004; G01N 21/3504; G01N 2201/1241; G01N 2201/12746
USPC ................................. 356/432–448, 213–236
See application file for complete search history.

(56) References Cited

U.S. PATENT DOCUMENTS

| | | | |
|---|---|---|---|
| 2010/0153048 A1 | 6/2010 | Myrick et al. | |
| 2011/0032516 A1 | 2/2011 | Zhou et al. | |
| 2014/0340684 A1* | 11/2014 | Edler | G01J 3/4338 356/409 |

\* cited by examiner

*Primary Examiner* — Tri T Ton

(74) *Attorney, Agent, or Firm* — Joseph Kolodka

(57) ABSTRACT

Aspects of the present disclosure describe gas sensor calibration methods and subsequent sensing methods employing same in conjunction with wavelength modulation spectroscopy (WMS). Additional aspects of the present disclosure advantageously employ WMS for highly-sensitive gas concentration measurement across a range of concentrations from ambient to a high concentration environment such as fire/smoke detection. Finally, still further aspects of the present disclosure determine and then employ two calibration factors and during measurement WMS-2f spectra to determine an inflection or "turning point" and subsequently which one of the two calibration factors to employ at a given concentration.

10 Claims, 8 Drawing Sheets

WAVELENGTH MODULATION SPECTROSCOPY GAS SENSOR CALIBRATION

CROSS REFERENCE TO RELATED APPLICATIONS

This application claims the benefit of U.S. Provisional Patent Application Ser. No. 62/514,036 filed 2 Jun. 2017 which is incorporated by reference as if set forth at length herein.

TECHNICAL FIELD

This disclosure relates generally to the chemical sensing of gases. More specifically, it pertains to a method of calibrating gas sensors for use with wavelength modulation spectroscopy.

BACKGROUND

As is known, the ability to reliably sense gas phase compositions is of considerable societal importance. For example, the ability to detect low concentrations of Carbon Monoxide (CO)—is particularly important in a household where its early detection may be a matter of life and death for household occupants as CO in sufficient concentration is lethal to those occupants.

Recently, laser spectroscopy—and in particular wavelength modulation spectroscopy (WMS) has proven to be both highly sensitive and highly accurate for gas phase detection. An essential component to the reliable detection of gas phase compositions is a calibrated detector. Unfortunately, traditional calibration methods for gas phase sensors used in WMS is generally unsuitable for high gas concentration environments frequently encountered. Consequently, methods that facilitate or otherwise improve the calibration and/or reliability of sensors for the detection of gas phase compositions throughout a wide range of gas phase concentration(s) would represent a welcome addition to the art.

SUMMARY

An advance in the art is made according to aspects of the present disclosure directed to a method of calibrating sensors used in gas phase detectors in conjunction with wavelength modulation spectroscopy.

In sharp contrast to the prior art, calibration method(s) according to the present disclosure advantageously employ two calibration factors thereby overcoming signal saturation effects characteristic of conventional, prior art calibration methods. During measurement, WMS-2f spectra is collected and a "turning point" or inflection point of that spectra is used to determine which of the two calibration factors is employed for gas concentration determination.

As we shall show and describe, calibration methods according to the present disclosure provide a range of calibrations including both linear and saturated regions of the gas detectors—heretofore unknown to the art.

As a result, gas sensors employed in WMS, calibrated according to aspects of the present disclosure, are useful for highly-sensitive gas sensing and high concentration gas measurement thereby advantageously enabling WMS techniques to be employed in a broader application set including ambient gas sensing and high gas concentration fire detection.

BRIEF DESCRIPTION OF THE DRAWING

A more complete understanding of the present disclosure may be realized by reference to the accompanying drawing in which:

FIG. 3 is a series of plots of WMS absorbance and 2f spectra at 2004 nm for $CO_2$ absorption peak illustrating when to employ calibration factors f2 and when to employ calibration factors f1 according to aspects of the present disclosure, wherein

Figure 1:
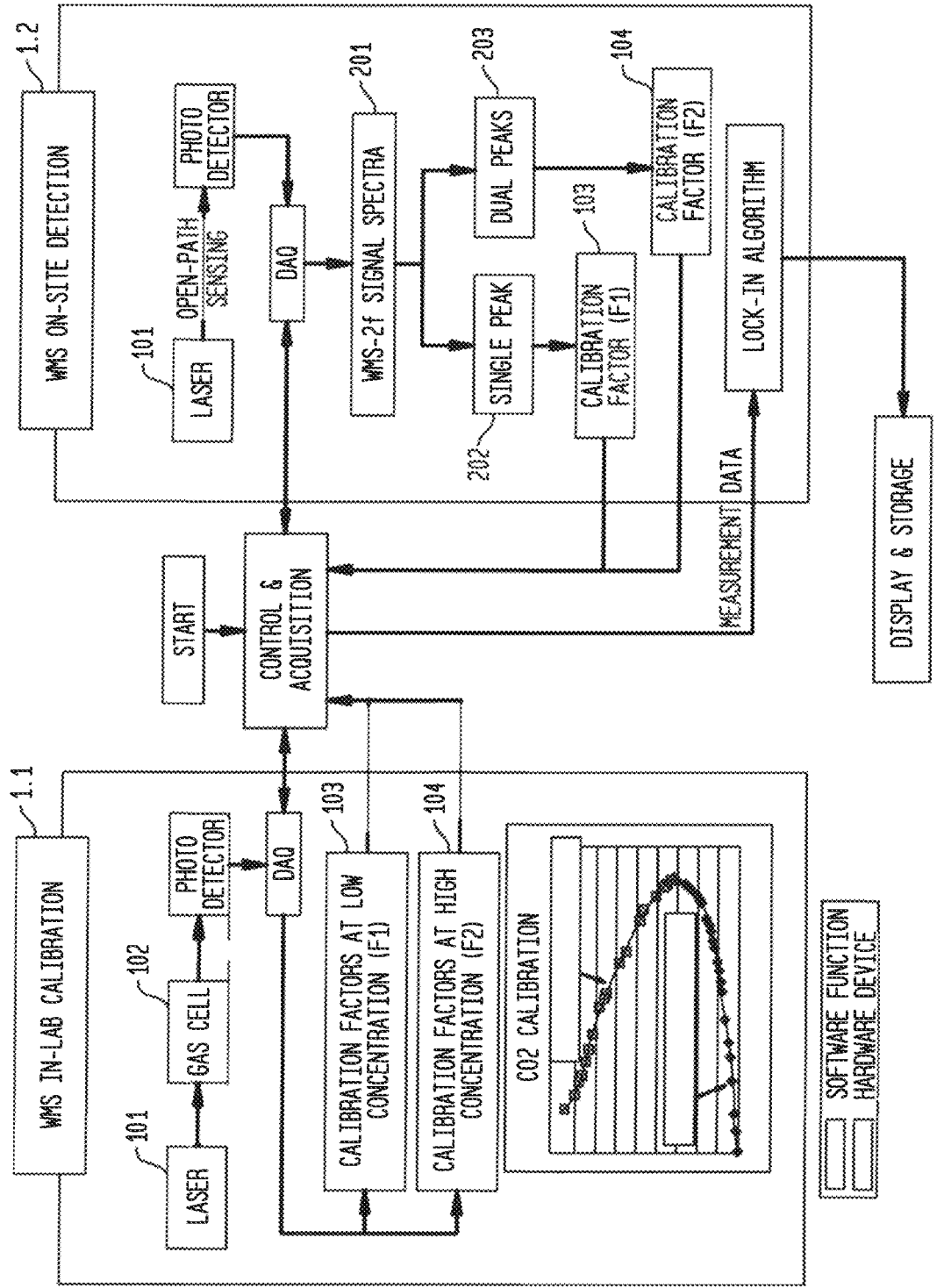
FIG. 1 is a schematic block/flow diagram of an illustrative gas calibration via WMS technique according to aspects of the present disclosure.

The illustrative embodiments are described more fully by the Figures and detailed description. Embodiments according to this disclosure may, however, be embodied in various forms and are not limited to specific or illustrative embodiments described in the drawing and detailed description.

DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are intended to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that any block diagrams herein represent conceptual views of illustrative circuitry embodying the principles of the disclosure.

Unless otherwise explicitly specified herein, the FIGS. comprising the drawing are not drawn to scale.

By way of some additional background, we begin by noting that over the last few decades, tunable diode laser (TDL) absorption spectroscopy has matured into a robust and convenient means of measuring a wide variety of gas parameters in difficult, real-world environments. Light emitted from robust, tunable diode sources is passed through a gaseous test sample to a detector, and the absorption of light can be related to gas temperature, pressure, species concentration, and velocity using spectral absorption models for the target absorbing species. For target species with discrete spectral-absorption features (e.g. small molecules and atoms)—where the absorption is wavelength-dependent over a short spectral window (a few $cm^{-1}$), the laser wavelength can be modulated sinusoidally and the nonuniform absorption gives rise to components in the detector signal at the harmonics of the original sinusoid frequency. The harmonic signals can be isolated with lock-in amplifiers (essentially band-pass filters), which greatly reduce the influence of laser and electronic noise by filtering out components of the detector signal outside of the harmonics. The harmonic signals can then be related back to the spectral absorption models for the target species and used to infer gas properties, but with much higher sensitivity than direct-absorption measurements.

Modulation spectroscopy is divided into two categories: frequency modulation spectroscopy (FMS) in which the modulation frequency is greater than the half-width of the probed absorption feature (100 MHz to several GHz range), and wavelength modulation spectroscopy (WMS) in which the modulation frequency is less than the optical frequency half-width of the probed absorption feature (kHz to several MHz range). Note that that high-frequency WMS (>100 kHz) offers excellent sensitivity without the burden of extremely fast detection electronics, as required by FMS. This is an important consideration for practical, field-deployable systems.

Recognizing the power of WMS for highly-sensitive measurements, many researchers have applied the technique to enable measurements in difficult environments that otherwise might not be possible with direct-absorption spectroscopy. Measurements in a high-pressure coal combustor, ground-test scramjet engines, and a variety of trace gas situations are just a few examples using WMS. A handheld methane leak detector and combustion measurements in a micro-gravity droptower are excellent examples of portable WMS systems where the sensor hardware itself is also compact, robust, and capable of operating in difficult environments.

One of the drawbacks to applying traditional WMS in practical environments for temperature and concentration measurements is the need to calibrate the WMS signals to a known mixture and condition (or a direct measurement of absorption) in order to recover the absolute concentration or temperature. Such calibration difficulties are further understood by knowing that typical calibrations of —$CO_2$—for example—are up to 3000 ppm while in operation the $CO_2$ levels experienced during fire detection—for example—can be much higher that that. In such common high gas concentration circumstances, traditional calibration method(s) are unsatisfactory.

As shall be shown and described, the present disclosure is directed to a calibration method for WMS gas sensors that advantageously overcome the problems associated with prior art calibration methods.

With reference now to FIG. 1, there is shown a schematic block/flow diagram illustrating WMS gas calibration/measurement/detection method(s) and structures according to aspects of the present disclosure. Note that as depicted in that figure, we have separated two aspects of the method(s) into an in-lab gas calibration (left side of FIG.—1.1) and an on-site detection (right side of FIG.—1.2).

Figure 2:
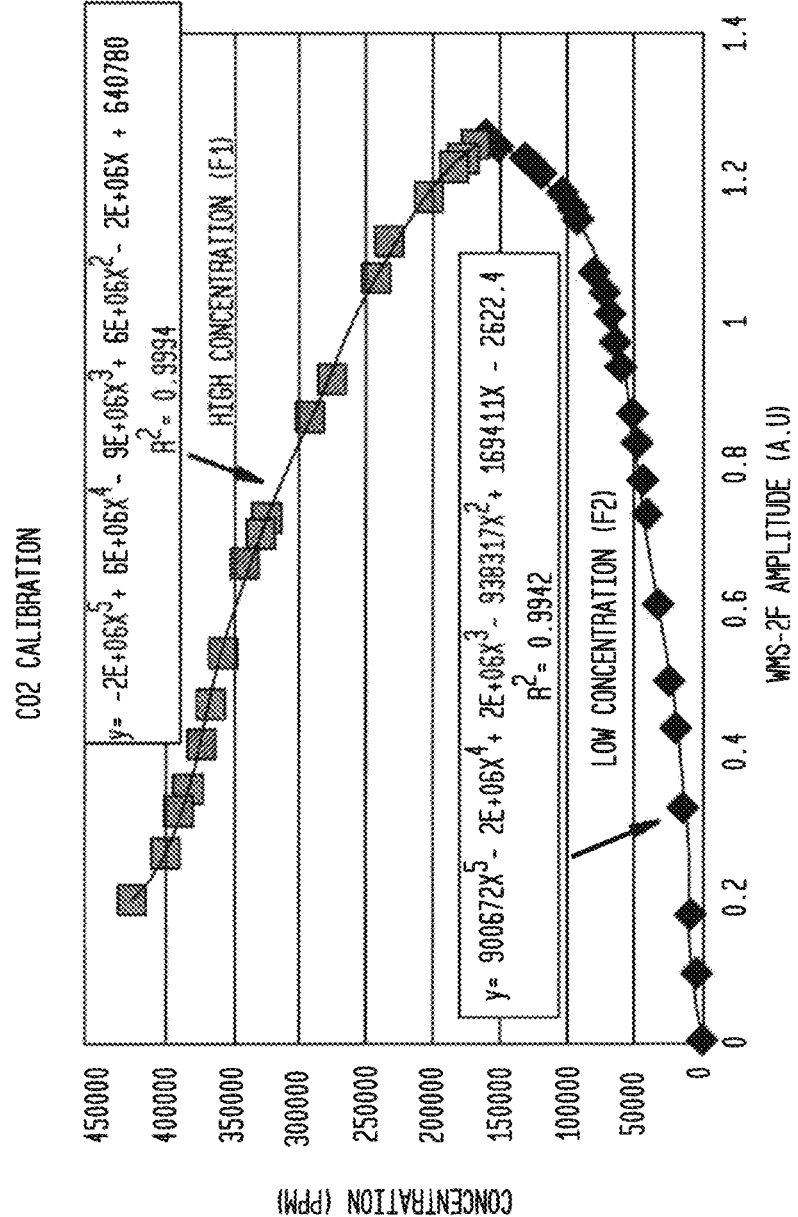
FIG. 2 is a plot of concentration (ppm) vs. WMS-2f amplitude (a.u.) for $CO_2$ calibration illustrating both high concentration regions (f2) and low concentration regions (f1) separated by inflection point according to aspects of the present disclosure.

At this point we note that one objective of the in-lab calibration process is the production of data relating gas concentration (ppm) to WMS-2f amplitude (a.u.). Such data when plotted produces a plot of $CO_2$ gas concentration vs WMS-2f amplitude as shown illustratively in FIG. 2. As we will describe in more detail, the plot of FIG. 2 is made over a very broad concentration (ppm) range from 0 to approximately 450000 ppm thereby including both very low and very high concentrations of the $CO_2$ gas.

With continued reference to FIG. 1, it may be observed that operationally, laser 101 emits optical energy that is directed through a gas cell 102 containing a sample gas and onto a photodetector assembly for data acquisition. The concentration of the gas is varied from very low to very high and from this data calibration factors at low concentration (f1) 103 and calibration factors at very high concentration (f2) 104 are made and stored by control and acquisition system.

Advantageously, the laser may be any of a variety depending upon the operational requirements. More particularly, the laser 101 may be distributed feed-back laser diode (DFB-LD) for $H_2S$, CO, $CO_2$ or $CH_4$ measurements or quantum cascade laser (QCL) for CO and $NH_3$ sensing—for example. Note further that we have only identified suitable, illustrative lasers in this text. Those skilled in the art will readily appreciate that any laser may be employed for these measurements—depending upon the particular operational characteristics desired of the laser so employed.

Note further that the gas cell 102 may likewise be any of a known type appropriate for the particular gas(es) and/or operational configurations. For example, fiber-coupled cell(s) or envelope type cell(s) use will depend upon the particular light source (laser) employed.

Likewise, the particular photodetector arrangement and data acquisitions system(s) employed are largely configuration dependent—and as will be readily appreciated by those skilled in the art—any of a number of known photodetector arrangements and data acquisition systems may be employed—according to aspects of the present disclosure.

As previously indicated, by measuring the WMS-2f amplitude at a plurality of concentrations of calibrated reference gas(es), a plot, such as that illustratively shown in FIG. 2 may be obtained from the known concentration/measured amplitude data.

With continued reference to that FIG. 2, we note that by measuring WMS-2f amplitude with the calibrated reference gases, calibration factors may be observed and determined. As shown in that figure, which is a plot of concentration (ppm) of $CO_2$ gas vs WMS-2f amplitude, the concentration of the gas is varied from 0 ppm to 450000 (45.5%) ppm and the WMS-2f amplitude is measured. Note that two regions of the resulting plot are identified namely, a low concentration (f2) region and a high concentration (f3). Operationally, the plot was obtained at a wavelength of 2004 nm and the concentration levels of the calibration gas is filled into a gas cell.

Note that the measured signal becomes saturated over 160000 ppm $CO_2$ and that the measured WMS-2f amplitude becomes smaller above these levels—even as the concentration increases. As shown in the figure, such transitions from unsaturated to saturated is coincident with an inflection point of the plot. Note that this inflection (turning) point is specific to the particular sensor employed.

According to aspects of the present disclosure—we advantageously separate calibration factors so determined into two separate ones—one for low concentration region(s) (f1—below 160000 ppm on FIG. 2 for $CO_2$) and one for high concentration region(s) (f2—above 160000 ppm on FIG. 2 for $CO_2$).

Figure 3A:
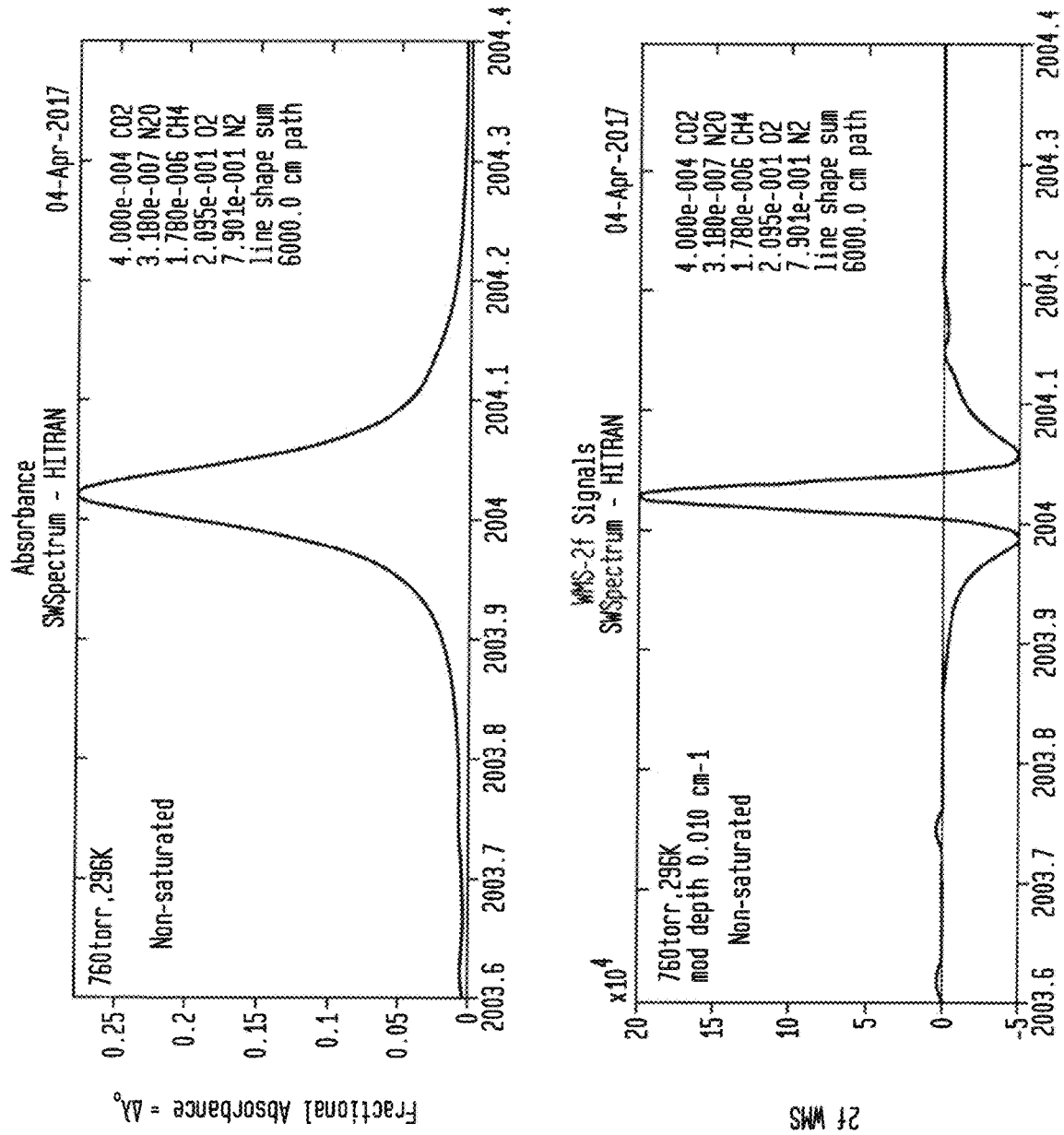
FIG. 3(A) shows in detail the WMS absorbance and WMS-2f signals for a non-saturated region that indicates employing calibration factors f2.

FIG. 3 is a series of plots of WMS absorbance and 2f spectra at 2004 nm for $CO_2$ absorption peak illustrating when to employ calibration factors f2 and when to employ calibration factors f1 according to aspects of the present disclosure, wherein FIG. 3(A) shows in detail the WMS absorbance and WMS-2f signals for a non-saturated region that indicates employing calibration factors f2; FIG. 3(B) shows in detail the WMS absorbance and WMS-2f signals for a close-to-saturated region that indicates employing calibration factors f2; FIG. 3(C) shows in detail the WMS absorbance and WMS-2f signals for a saturated I region that indicates employing calibration factors f1; and FIG. 3(D) shows in detail the WMS absorbance and WMS-2f signals for a saturated II region that indicates employing calibration factors f2; all according to aspects of the present disclosure.

With reference to FIG. 3, we note that as schematically illustrated therein, we may observe that for those regions either non-saturated or close-to-saturated (the upper two absorbance and WMS-2f signal plots), we employ calibration factors f2 according to aspects of the present disclosure. Conversely, for those regions that are saturated (the lower two absorbance and WMS-2f signal plots), we employ calibration factors f1.

Figure 3B:
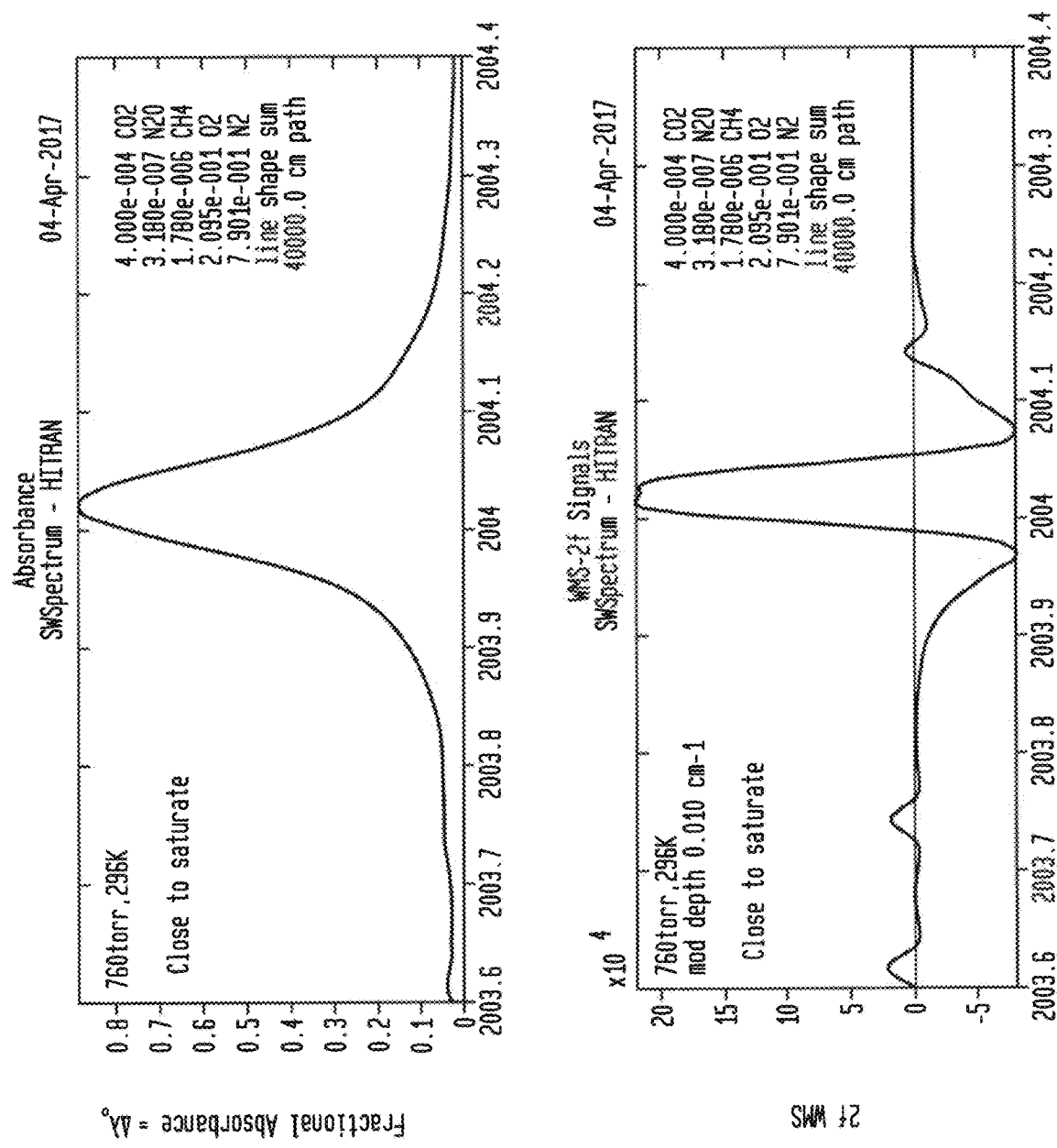
FIG. 3(B) shows in detail the WMS absorbance and WMS-2f signals for a close-to-saturated region that indicates employing calibration factors f2.
Figure 3C:
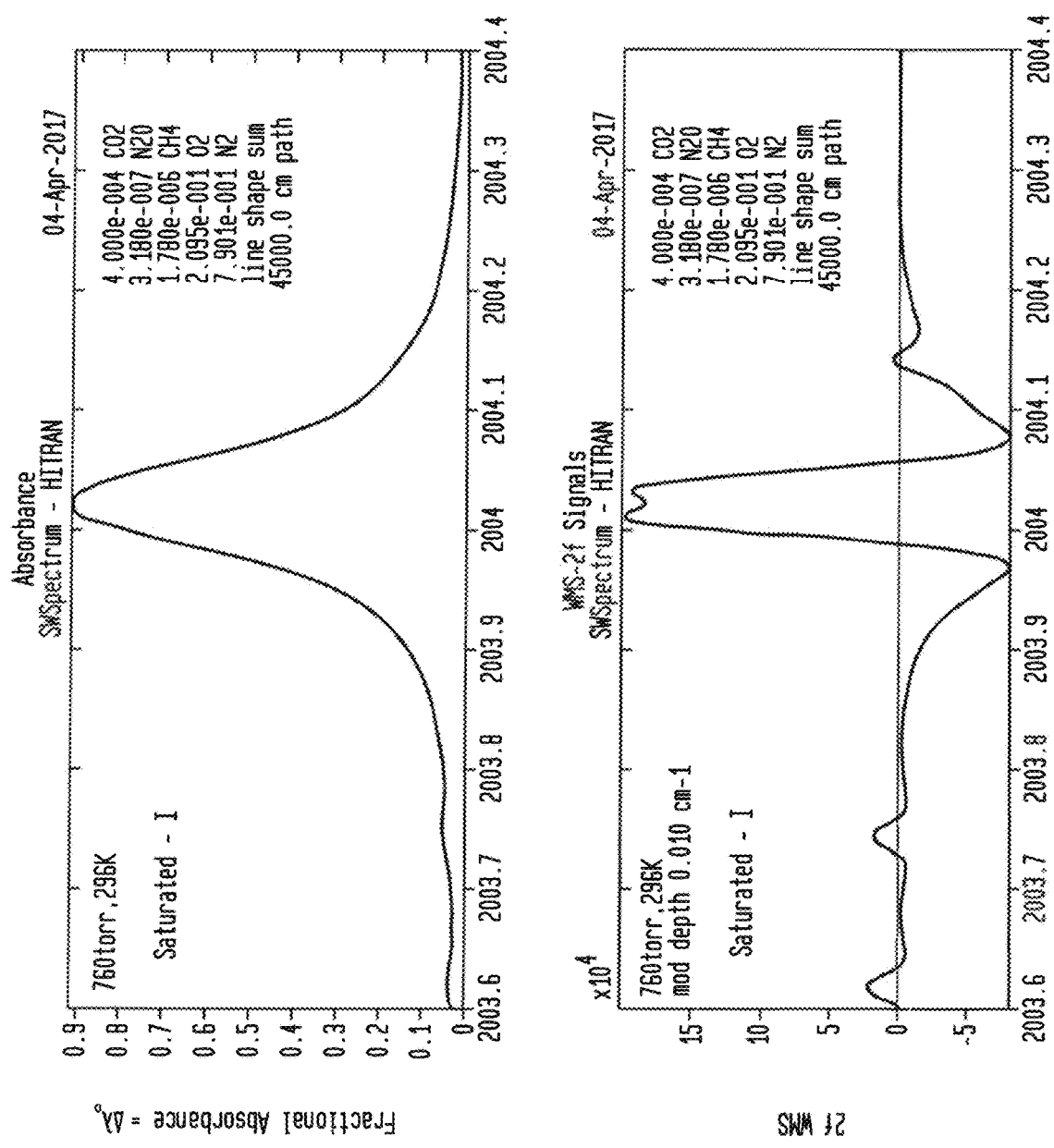
FIG. 3(C) shows in detail the WMS absorbance and WMS-2f signals for a saturated I region that indicates employing calibration factors f1.
Figure 3D:
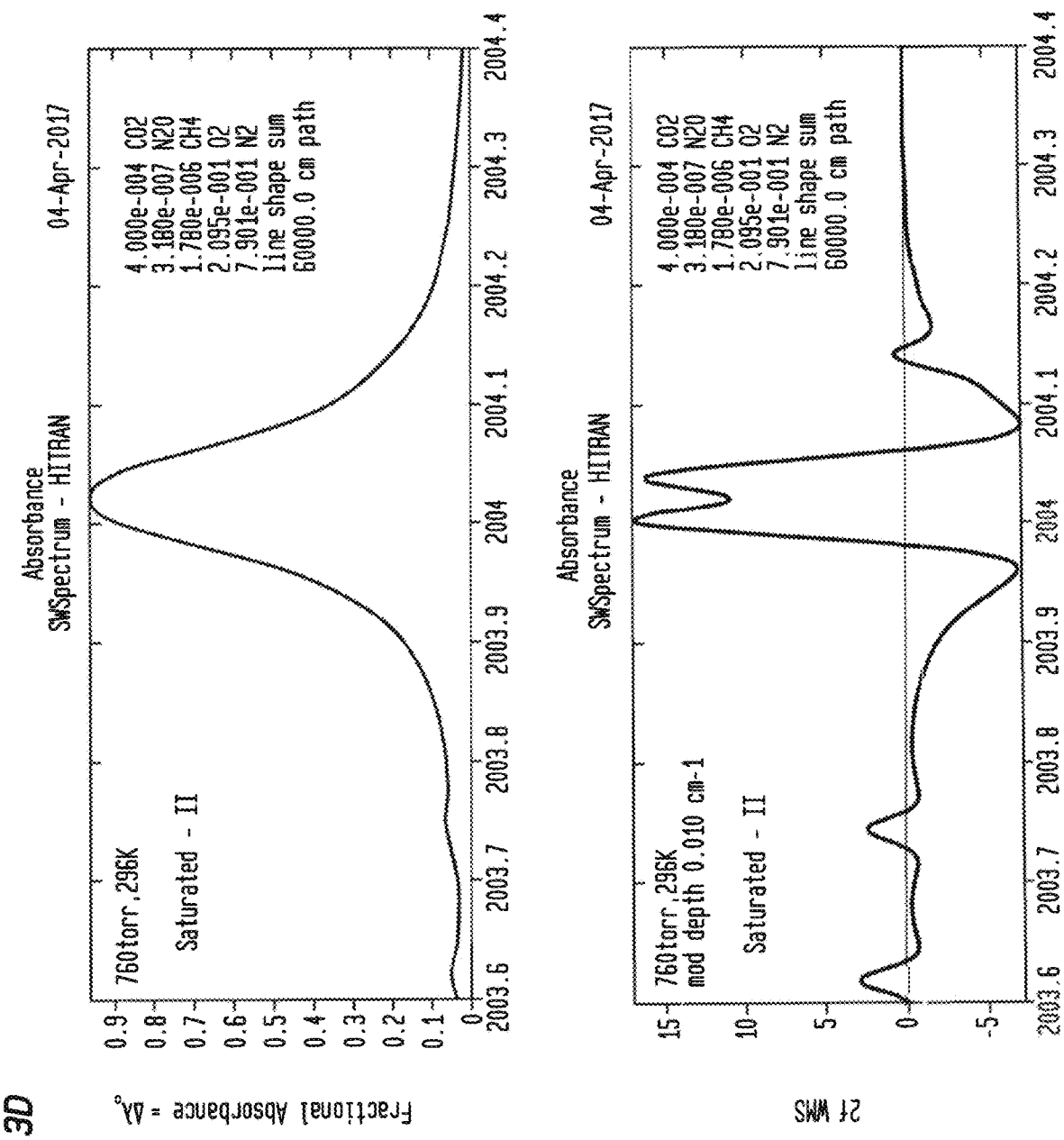
FIG. 3(D) shows in detail the WMS absorbance and WMS-2f signals for a saturated II region that indicates employing calibration factors f2; all according to aspects of the present disclosure.

FIG. 3(A) shows in detail the WMS absorbance and WMS-2f signals for a non-saturated region that indicates employing calibration factors f2; FIG. 3(B) shows in detail the WMS absorbance and WMS-2f signals for a close-to-saturated region that indicates employing calibration factors f2; FIG. 3(C) shows in detail the WMS absorbance and WMS-2f signals for a saturated I region that indicates employing calibration factors f1; and FIG. 3(D) shows in detail the WMS absorbance and WMS-2f signals for a saturated II region that indicates employing calibration factors f2; all according to aspects of the present disclosure.

Note that for low concentrations wherein calibration factors f2 are employed—the WMS-2f signals exhibit a single peak (FIG. 3(A), FIG. 3(B)). Conversely, for high concentrations wherein calibration factors f1 are employed—the WMS-2f signals exhibit a double (two) peaks (FIG. 3(C), FIG. 3(D)). Note further that for the turning (inflection) point of FIG. 2, the plot(s) of FIG. 3(B) show the absorbance and WMS-2f signals, respectively.

Figure 4:
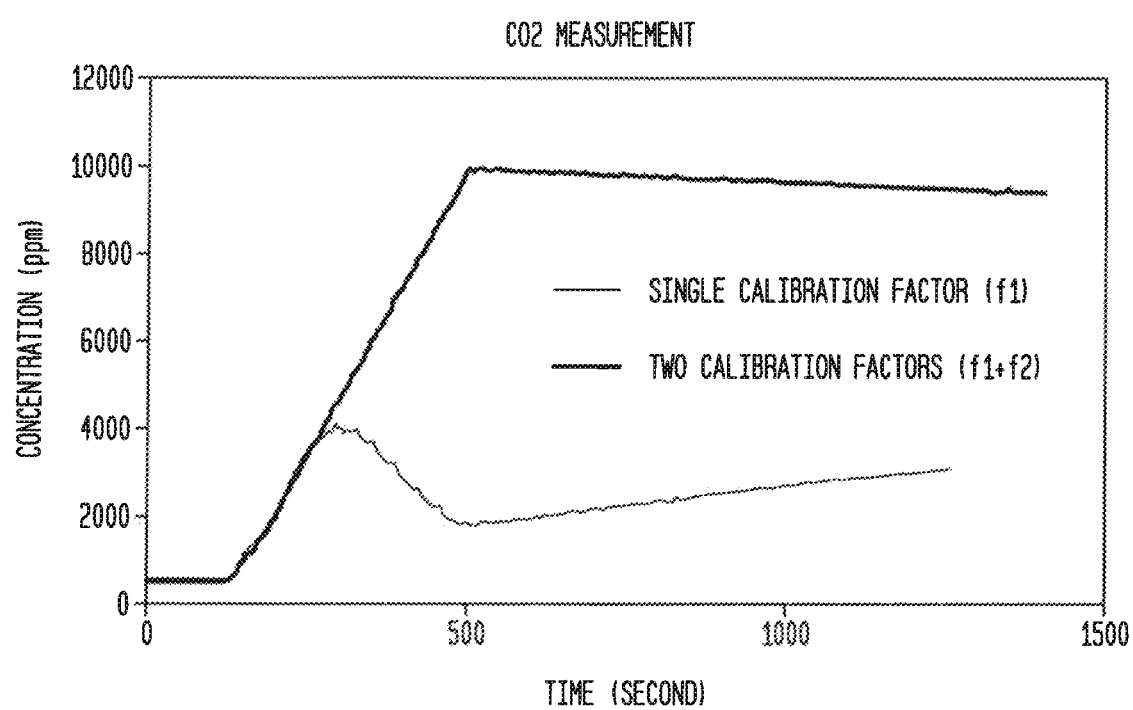
FIG. 4 is a plot of concentration (ppm) vs. time (seconds) for $CO_2$ using a single calibration factor and two factors according to aspects of the present disclosure.

FIG. 4 is a plot of concentration (ppm) vs. time (seconds) for $CO_2$ using a single calibration factor and two factors according to aspects of the present disclosure. As may be observed from that figure, concentration measurements employing single calibration factors are much less useful over a broad range of concentrations such as that illustratively shown in this figure as compared with two calibration factors employed over the same broad range.

Figure 5:
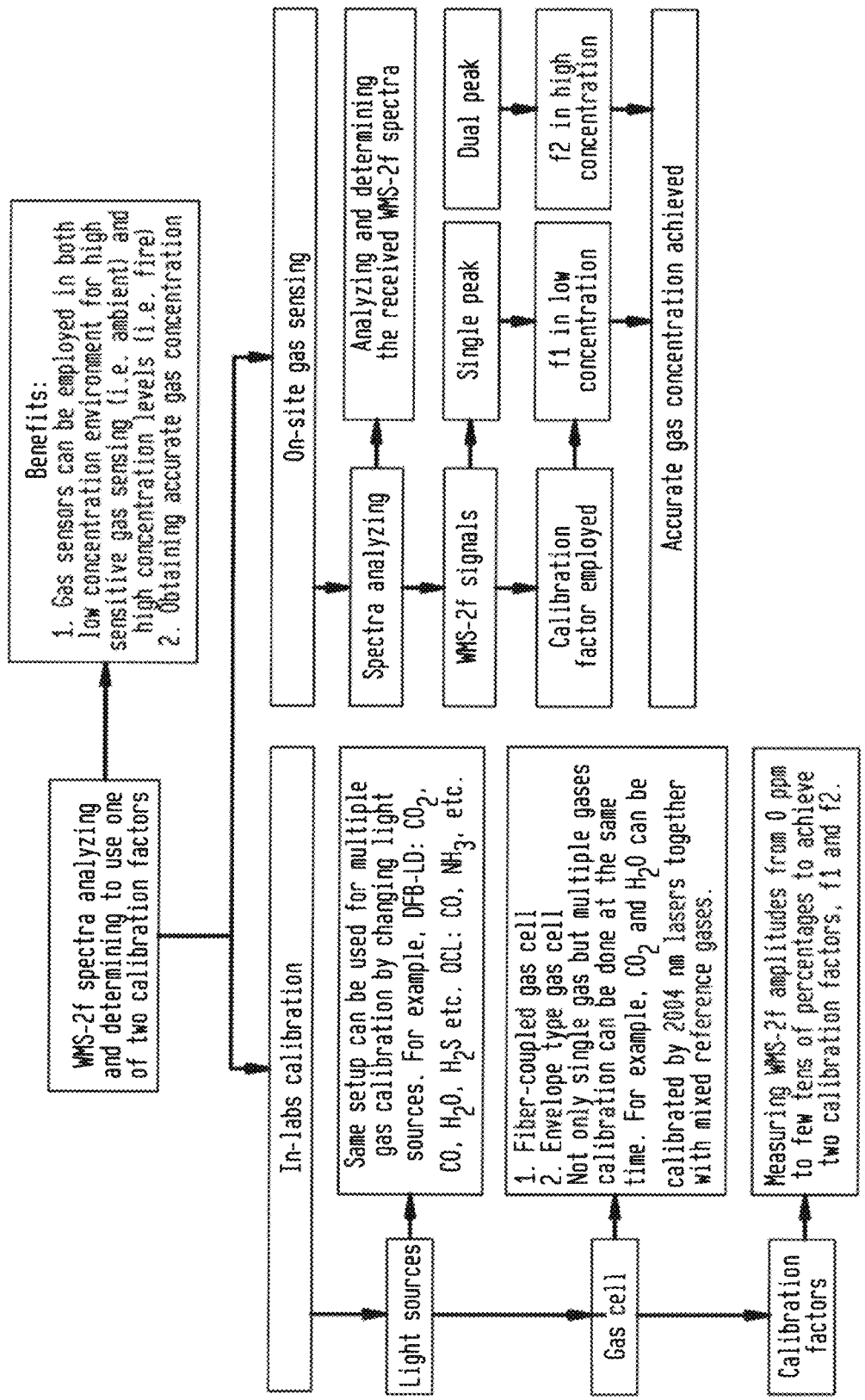
FIG. 5 is a flow diagram illustrating an overview of an illustrative calibration process and in-field measurement according to aspects of the present disclosure.

FIG. 5 is a flow diagram illustrating an overview of an illustrative calibration process and in-field measurement according to aspects of the present disclosure.

With reference to that figure, we again note that while WMS is a highly sensitive measurement technique it is generally not suitable for high concentration gas sensing as signals are saturated in such high gas concentration levels. According to aspects of the present disclosure however, gas sensors calibrated according to the present disclosure may be advantageously employed in WMS for both low and high gas concentration environments.

Operationally, an in-lab calibration is performed wherein a light source (laser) is used to illuminate gas in a suitable gas cell and a set of calibration factors are determined wherein those calibration factors for WMS-2f amplitude measurements include one for low concentrations and one for high concentrations of the gas. Once such calibration is performed, on-site (in field) gas sensing involves collecting/analyzing WMS-2f spectral amplitudes and employing the appropriate calibration factor for the particular concentration being measured. In particular, when a WMS-2f measured amplitude exhibits a single peak, the first calibration factor—for low concentrations—is employed, while when the WMS-2f measured amplitude exhibits a dual peak, the second calibration factor—for high concentrations—is employed. In this inventive manner, accurate gas concentrations may be measured and determined over the very broad range of concentrations that may be encountered. Such high concentration measurement is particularly important and applicable to CO detection as part of fire/smoke detection where differences between ambient an fire conditions may be several orders of magnitude of concentration.

At this point, while we have presented this disclosure using some specific examples, those skilled in the art will recognize that our teachings are not so limited. Accordingly, this disclosure should be only limited by the scope of the claims attached hereto.

The invention claimed is:

1. A wavelength modulation spectroscopy (WMS) gas sensor calibration and detection method comprising:
    measuring WMS-2f amplitudes for a gas over a range of known concentrations;
    identifying, from the measured amplitudes, a first calibration factor (f1) for low concentrations of the gas and a second calibration factor (f2) for high concentrations of the gas;
    generating a WMS-2f signal spectra for an unknown concentration of the gas;
    determining whether the generated WMS-2f signal spectra exhibits a single peak or dual peaks; and
    selecting one of the identified calibration factors f1 or f2 based on the number of peaks determined.

2. The method of claim 1 further comprising:
    determining, using the selected calibration factor, the concentration of the gas whose concentration was unknown.

3. The method of claim 2 further comprising:
    displaying and storing the determined concentration.

4. The method of claim 3 wherein the first calibration factor (f1) and the second calibration factor (f2) are identified by their position(s) relative to an inflection point on a graph of the measured WMS-2f amplitudes.

5. The method of claim 3 wherein the gas of unknown concentration is Carbon Dioxide gas ($CO_2$).

6. A wavelength modulation spectroscopy (WMS) gas sensing system comprising:
    a light source;
    a gas cell through which light emitted from the source is directed;

a detector that measures light that passes though the cell; and an acquisition and control system that:
- measures WMS-2f amplitudes for a gas contained in the cell over a range of known concentrations;
- identifies, from the measured amplitudes, a first calibration factor (f1) for low concentrations of the gas and a second calibration factor (f2) for high concentrations of the gas;
- generates a WMS-2f signal spectra for an unknown concentration of the gas;
- determines whether the generated WMS-2f signal spectra exhibit a single peak or dual peaks; and
- selects one of the identified calibration factors f1 or f2 based on the number of peaks determined.

7. The system of claim 6 wherein the acquisition and control system:
determines, using the selected calibration factor, the concentration of the gas whose concentration was unknown.

8. The system of claim 7 wherein the acquisition and control system:
displays and stores the determined concentration.

9. The system of claim 8 wherein the first calibration factor (f1) and the second calibration factor (f2) are identified by their position(s) relative to an inflection point on a graph of the measured WMS-2f amplitudes.

10. The system of claim 9 wherein the gas of unknown concentration is Carbon Dioxide gas ($CO_2$).

* * * * *